United States Patent [19]

Greeff et al.

[11] Patent Number: 5,190,530
[45] Date of Patent: Mar. 2, 1993

[54] INFLATABLE CANNULA RETAINING DEVICE

[75] Inventors: Susan M. J. A. Greeff; Janice A. Guastella, both of Cape Province, South Africa

[73] Assignee: OP-CO Medical Products Limited, New York, N.Y.

[21] Appl. No.: 599,871

[22] Filed: Oct. 19, 1990

[30] Foreign Application Priority Data

Oct. 20, 1989 [ZA] South Africa .................. 89/7969

[51] Int. Cl.⁵ .............................................. A61M 5/32
[52] U.S. Cl. .................................... 604/179; 604/174
[58] Field of Search ............... 128/DIG. 20, DIG. 26, 128/877, 878, 77, 89 R, 87 R; 604/179, 174; 602/13

[56] References Cited

U.S. PATENT DOCUMENTS

| | | | |
|---|---|---|---|
| 3,242,923 | 3/1966 | Jacoby, Sr. | 128/DIG. 20 |
| 3,930,496 | 1/1976 | Gibbons | 128/DIG. 20 |
| 4,182,320 | 1/1980 | Sweeney | 128/DIG. 20 |
| 4,301,791 | 11/1981 | Franco, III | 128/DIG. 20 |
| 4,396,018 | 8/1983 | Sibley | |
| 4,470,410 | 9/1984 | Elliott | 128/877 |
| 4,649,913 | 3/1987 | Watson | |
| 4,941,479 | 7/1990 | Russell et al. | 128/877 |

FOREIGN PATENT DOCUMENTS 276712 2/1965 Australia .
1497441 1/1978 United Kingdom .

Primary Examiner—John J. Wilson
Assistant Examiner—Jeffrey A. Smith
Attorney, Agent, or Firm—Lane & Mittendorf

[57] ABSTRACT

A protective cannula retaining device provides a medical accessory comprising an inflatable pad having an observation opening and a transparent strap positioned over the opening.

5 Claims, 3 Drawing Sheets

INFLATABLE CANNULA RETAINING DEVICE

FIELD OF INVENTION

This invention relates to a medical accessory.

BACKGROUND OF INVENTION

Fluid delivery to a patient through an intravenous cannula suffers from the disadvantage that the cannula may become dislodged. Adhesive tape is commonly employed to secure the cannula in position, but with such an arrangement the intravenous site is obscured and inspection of the site to ensure that the cannula is correctly inserted, is not possible.

OBJECT OF THE INVENTION

It is accordingly an object of the present invention to provide a novel medical accessory suitable for securing a cannula or the like at the intravenous site. It is a further object of the invention to immobilize the limb of a patient in the zone of such an intravenous site.

SUMMARY OF INVENTION

According to the invention there is provided a medical accessory which comprises an inflatable envelope having an opening or window therein.

The envelope may be in the form of a annular cuff or sleeve which is able to fit on an arm or a leg of a patient.

Alternatively, the envelope may be provided with straps or strap-like elements whereby the envelope can be tied in position on a patient.

Further according to the invention the envelope may be formed by inner and outer sheets of weldable plastics material defining between them an inflatable cavity, the opening or window being formed by the inner and outer sheets having been welded together along a weld line forming a closed loop, and the sheet material in the region bounded by the weld line having been removed.

The sheet material may be a transparent or semi-transparent material.

There may be a plurality of openings or windows in the envelope.

A non-return valve may be provided to enable the pad to be inflated.

The accessory may include a flap for closing the opening or window if desired.

In one arrangement in accordance with the invention a stiffening board or the like will be provided to extend substantially along the length of the envelope. Preferably the envelope will include a pocket which is adapted removably to receive the stiffening board.

BRIEF DESCRIPTION OF THE DRAWINGS

The invention will now be described in more detail, by way of example, with reference to the accompanying drawings.

In the drawings.

DETAILED DESCRIPTION OF THE INVENTION

Figure 1:
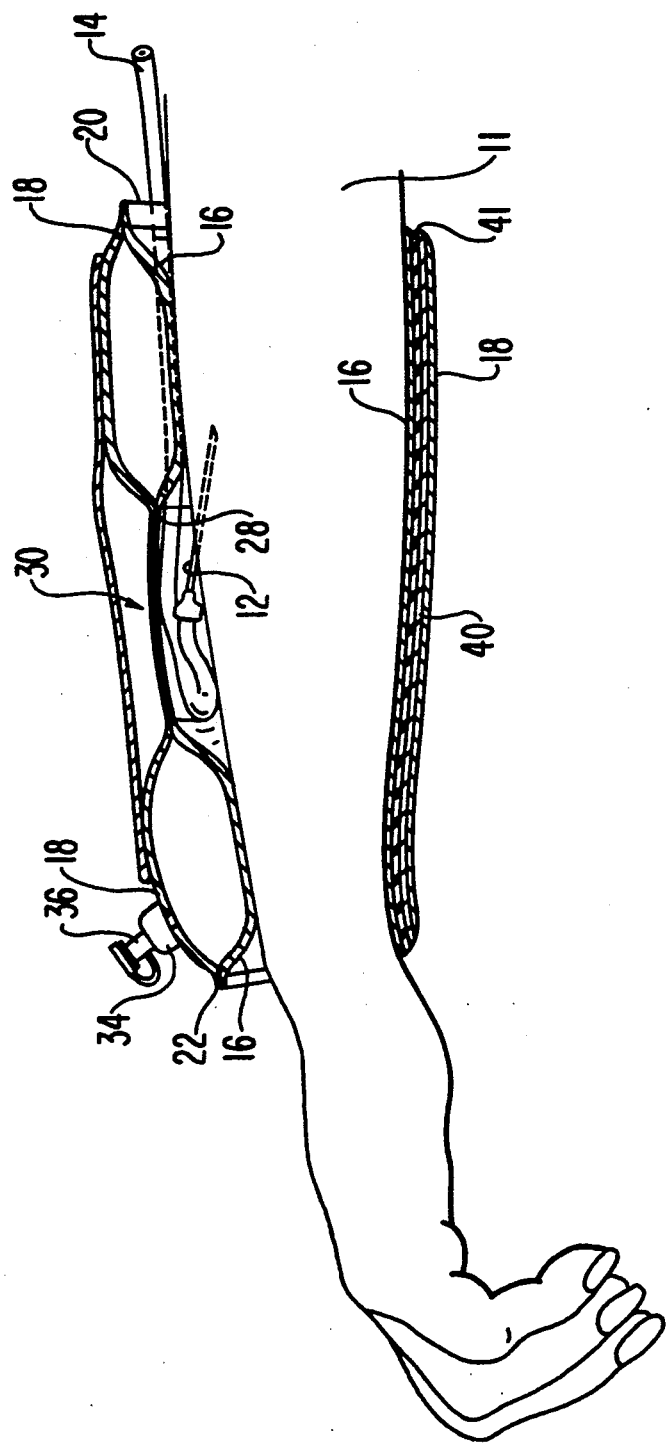
FIG. 1 illustrates a medical accessory in accordance with the invention, in position on the arm of a patient, the device itself being shown in section.

Referring now to the drawings in more detail, reference numeral 10 generally indicates a medical accessory device, the device being shown in position on the arm 11 of a patient. The device is in the form of an inflatable cuff or sleeve which extends around the arm 11, and is used to protect and hold in position an intravenous cannula 12 and an intravenous line 14 leading to the cannula.

The device 10 is formed by inner and outer sheets 16 and 18 respectively, of a weldable plastic material. The plastic material may, for example, be PVC material. The material will preferably be semi-transparent or translucent.

The sheets 16 and 18 are welded together along edges 20 and 22 thereof, and sides 24 and 26 to form the sheets 16 and 18 into a hollow, annular sleeve or cuff. In the arrangement illustrated, the annular sleeve is divided into an inflatable roof portion and a floor portion which contains a stiffening board 40 and which will in most instances be non-inflatable. The stiffening board could for example be of cardboard material with a layer of foam material 41 thereon. The stiffening board 40 will be removable from the sleeve when not required, through a slit, not shown, in one of the base panels of the sleeve. It would be appreciated that the stiffening board 40 has the advantage of immobilizing a joint of a patient for example where a cannula 12 is to be inserted at the elbow zone or wrist zone of a patient.

The sheets 16 and 18 are further welded together along a number of weld lines 28, each of the weld lines 28 forming a closed loop, and the sheet material in the region bounded by each of the weld lines removed to form an opening. One of these openings, designated 30, is of elongate form, extending in the axial direction of the cuff or sleeve. The other openings, each designated 32, are round and somewhat smaller than the opening 30, and are adapted to provide ventilation.

A non-return valve 34 having a stopper 36 is provided to enable the device to be inflated.

Figure 2:
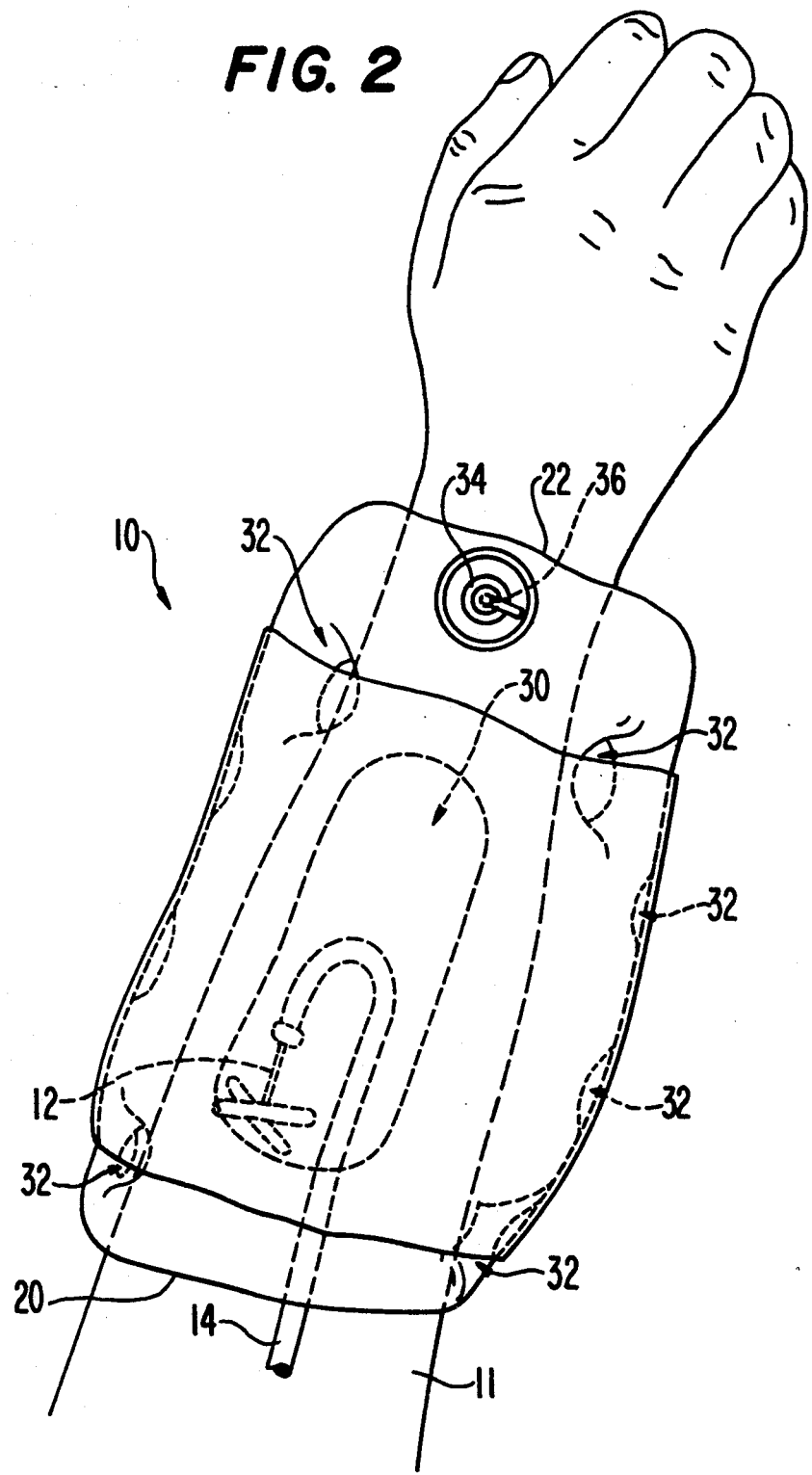
FIG. 2 is a view of the device from above, again shown in position on the arm of a patient.
Figure 3:
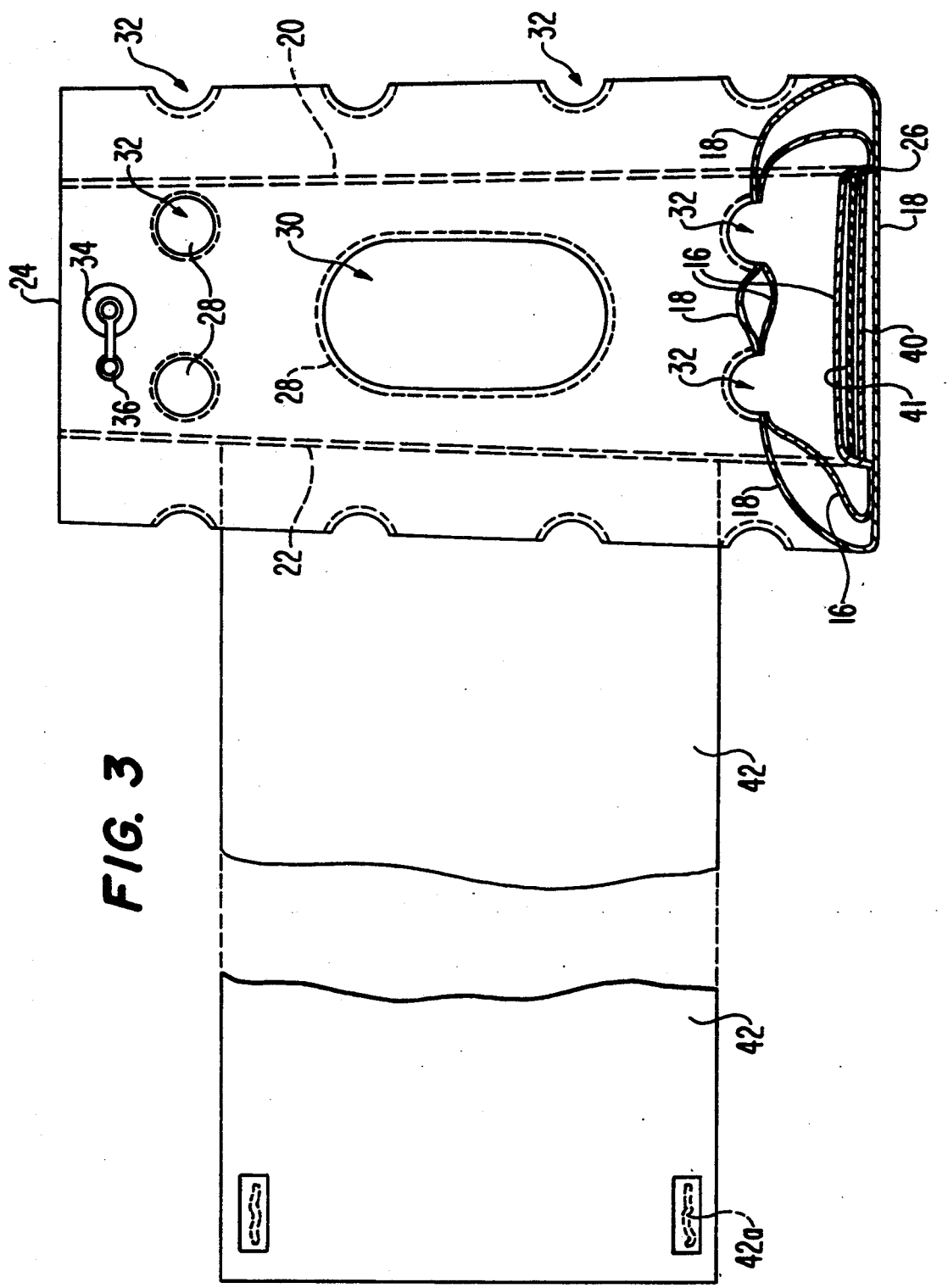
FIG. 3 shows the device in an opened and folded flat condition.

In use, the device 10 is placed in position on the arm 11 while in an uninflated condition, and is then inflated via the valve 34. If desired, the device may be inflated by means of a straw which fits into the valve 34. Inflation will cause the device to expand as shown in FIGS. 1 and 2, and this will cause the device to be held gently in position on the arm 11.

The cannula 12 can be inserted into the arm either before or after placing the device 10 in position.

The intravenous line 14 can extend through the opening 30. Alternatively, the intravenous line can extend between the layer 18 and the patient's arm as shown.

If desired, a flap 42 may be provided, the flap 42 being secured to the cuff or sleeve along a side 24 or 26. The free end of the flap 42 can be removably secured to the opposite side 24 or 26 by adhesive patches 42a, so as to close the opening 30 and thus protect the cannula 12 and the intravenous line 14. The opening 30 forms a hollow surrounding the drip site, protecting the cannula 12 and the intravenous line 14 against disturbance. If the flap 42 is transparent or translucent, good drip site visibility is maintained even when the flap is closed.

If desired, the cardboard stiffener 40 could be inserted between the arm 11 and the inside of the cuff or sleeve, on the side opposite the cannula 12. In an alternative arrangement the stiffener 40 can be dispensed and the floor portion formed as a roof portion to be inflatable and provided with appertures 32.

Instead of the non-return valve 34, the device may be provided with an integrally formed tube having a mouthpiece at the end thereof. Such a device will be inflated by blowing into the mouthpiece and then tying the tube closed. When the device is to be removed the tube can simply be cut, allowing the air to escape, and the device then discarded.

In a further alternative construction (not shown), the device may be in the form of an inflatable pad having an opening such as the opening 30 therein, the pad being provided with a number of straps which enable it to be tied to the body of a patient. For example, such a device could be used where an intravenous cannula is to be inserted into the sub-clavian vein of the patient, one pair of straps being tied around the neck of the patient and another pair of straps being tied underneath the patient's arm. In an alternative application, the straps could be used to adjust the diameter of the sleeve shown in the drawings and with such an arrangement, the sleeve could be formed with a longitudinal split or overlap zone.

In yet a further alternative construction, for use on the head of a patient, e.g. where it is desired to insert an intravenous cannula into the scalp of an infant, the device may be in the form of a hood which can be placed on the head of the patient. The device may also be in the form of a shoe, for use in cases where it is desired to insert an intravenous cannula into the foot of the patient.

It will be appreciated that a device such as described above could also be used on its own, i.e. without the intravenous cannula and the intravenous line, for example in the treatment of phlebitis.

We claim:

1. A protective medical retaining device for use with cannula means having connected intravenous line means, said cannula means being inserted in a patient, with said retaining device providing immobilization and protection for said cannula means with connected intravenous line means, said retaining device comprising:

an inflatable pad means for covering skin of said patient adjacent said cannula means, said inflatable pad means including at least one observation opening that can be positioned over said cannula means so said cannula means is positioned within said observation opening, said inflatable pad means including strap means for retaining said inflatable pad means adjacent said skin of said patient, said cannula means being immobilized with respect to said skin of said patient when said inflatable paid means is inflated wherein said strap means is transparent and said strap means is positioned over said observation opening to provide an observation window means over said cannula means.

2. A method for protecting, immobilizing and observing cannula means with connected intravenous line means inserted in a patient, comprising the steps of:

positioning on a limb of said patient adjacent to said cannula means an inflatable annular sleeve means with at least one observation opening in said inflatable annular sleeve means;

positioning said observation opening so said cannula means is within said observation opening; and inflating said inflatable annular sleeve means so said cannula means with connected intravenous line means is immobilized with respect to skin of said patient.

3. The method for protecting, immobilizing and observing cannula means according to claim 2, including the step of:

applying transparent flap means over said observation opening to provide an observation window.

4. A method for protecting, immobilizing and observing cannula means with connected intravenous line means inserted in a patient, comprising the steps of:

positioning on said patient adjacent to said cannula means an inflatable pad means with at least one observation opening in said inflatable pad means;

positioning said observation opening so said cannula means is within said observation opening;

attaching strap means to said inflatable pad means for retaining said inflatable pad means adjacent said skin of said patient; and, inflating said inflatable pad means so said cannula means with connected intravenous line means is immobilized with respect to said skin of said patient.

5. The method for protecting, immobilizing and observing cannula means according to claim 4, including the step of:

applying transparent flap means over said observation opening to provide an observation window.

* * * * *